US010154681B2

(12) United States Patent
Cohen

(10) Patent No.: US 10,154,681 B2
(45) Date of Patent: Dec. 18, 2018

(54) GOITROGEN-FREE BEVERAGE, METHODS OF USE AND METHOD OF FORMULATING THE SAME

(71) Applicant: Script Essentials, LLC, Broomfield, CO (US)

(72) Inventor: Suzy Cohen, Broomfield, CO (US)

(73) Assignee: Script Essentials, LLC, Broomfield, CO (US)

( * ) Notice: Subject to any disclaimer, the term of this patent is extended or adjusted under 35 U.S.C. 154(b) by 0 days.

(21) Appl. No.: 15/342,210

(22) Filed: Nov. 3, 2016

(65) Prior Publication Data

US 2017/0127701 A1     May 11, 2017

Related U.S. Application Data

(60) Provisional application No. 62/251,966, filed on Nov. 6, 2015.

(51) Int. Cl.
| | | |
|---|---|---|
| *A23L 2/52* | (2006.01) | |
| *A61K 36/05* | (2006.01) | |
| *A61K 36/23* | (2006.01) | |
| *A61K 36/73* | (2006.01) | |
| *A61K 36/88* | (2006.01) | |
| *A23L 33/105* | (2016.01) | |
| *A23L 33/135* | (2016.01) | |
| *A61K 36/899* | (2006.01) | |

(52) U.S. Cl.
CPC .............. *A23L 2/52* (2013.01); *A23L 33/105* (2016.08); *A23L 33/135* (2016.08); *A61K 36/05* (2013.01); *A61K 36/23* (2013.01); *A61K 36/73* (2013.01); *A61K 36/88* (2013.01); *A61K 36/899* (2013.01); *A23V 2002/00* (2013.01)

(58) Field of Classification Search
CPC ........ A23L 2/52; A23L 33/105; A23L 33/135; A61K 36/05; A61K 36/23; A61K 36/73; A61K 36/88; A61K 36/899; A23V 2002/00

USPC ........................................................ 435/183
See application file for complete search history.

(56) References Cited

U.S. PATENT DOCUMENTS

2009/0104312 A1*  4/2009  Kamarei .................. A23L 2/02
                                                                426/72

OTHER PUBLICATIONS

Lucky Vitamin, Nature's Plus Whole Food Total Body Cleanse, Available online at: www.luckyvitamin.com/p-33078-nature-s-plus-whole-food-total-body-cleanse-with-acai-exotic-superfruits-168-vegetarian-capsules?redirect=1, Available as early as Aug. 16, 2010 per the oldest review.*
Rainforest Foods, Do you know your Wheatgrass from you Barley Grass?, Feb. 6, 2010, Available online at: www.rainforestfoods.com/blog/wheatgrass-versus-barley-grass/.*
Dictionary.com, Organic, Available online at: www.dictionary.com/browse/organic?s=t, Accessed Jan. 29, 2018.*
Cohen "Thyroid Healthy, Lose Weight, Look Beautiful and Live the Life You Imagine," Dear Pharmacist Inc., Apr. 2014, 304 pages (155, 191-199, 207-211, 216-219).

* cited by examiner

*Primary Examiner* — Jennifer M. H. Tichy
(74) *Attorney, Agent, or Firm* — Lewis Brisbois Bisgaard & Smith LLP; Ian R. Walsworth

(57) ABSTRACT

The present disclosure relates to a compound, method of making the compound, method of using such compound preferably in the form of a dietary supplement that, when administered, is capable of use by any individuals, including patients having thyroid disease or various thyroid-related disorders. The unique combination of the composition is preferably administered orally, and preferably in the form of a drink. In some embodiments, the composition includes at least organic *chlorella*, organic dulse, organic acai, organic carrot, organic pineapple, apple pectin, organic inulin, PR-4 probiotic strain—preferably "*Bacillus Coagulans*," organic wheat grass, organic beet root, organic ulva, organic evaporated cane juice, natural flavorsweet flavor, sodium chloride, citric acid, organic guar gum, creamy vanilla flavor, natural raspberry flavor, and natural mixed berry flavor.

25 Claims, No Drawings

GOITROGEN-FREE BEVERAGE, METHODS OF USE AND METHOD OF FORMULATING THE SAME

CROSS-REFERENCE TO RELATED APPLICATIONS

This application claims the benefit of U.S. Provisional Patent Application No. 62/251,966, filed Nov. 6, 2015, the entire disclosure of which is incorporated herein by reference.

FIELD OF THE INVENTION

The present invention is directed to beverages, particularly green drinks and super foods, and methods for formulating the same.

BACKGROUND OF THE INVENTION

The human thyroid gland naturally produces the hormones thyroxine (T4) and triiodothyronine (T3), which are essential to the proper development and functions of cells in the human body. Thyroid hormones regulate the metabolism of fats, proteins and carbohydrates. In turn, thyroid hormones affect how these compounds produce energy. In addition to these functions, thyroid hormones have several critical functions in the human body, especially pertaining to human metabolic and cardiovascular systems. For example, production of T4 supports cardiac output, a healthy heart rate, respiratory rate, and basal metabolic rate (BMR).

There are presently a number of known but unresolved problems relating to the human thyroid, general thyroid disease and thyroid-related disorders. By way of example, a low BMR may cause a person to feel cold, fatigued and retain weight. Other problems are known to those of ordinary skill in the art. Therefore, it is desirable to provide a compound, which addresses these problems and otherwise improves upon the healthy function of the human thyroid gland.

There are also disadvantages with many dietary supplements, energy drinks, green drinks and other consumables designed to promote a healthy thyroid. For example, many commercially available products promote thyroid health, yet contain either goitrogens, fluorides, or both. Goitrogenic foods, including broccoli, cabbage, kale, alfalfa, grasses, seaweeds, etc., attack the thyroid gland and reduce production of thyroid hormone. Fluorides can damage healthy thyroid production by reducing iodine uptake, and can cause additional effects that limit utilization of thyroid hormones. The problem exists that all other greens formulas contain goitrogenic foods, or fluoride-containing foods, which attack thyroid hormone production.

These problems and others are addressed by the compositions and methods described in detail below.

SUMMARY OF THE INVENTION

In varying embodiments described herein, the invention relates to a dietary supplement that is capable of use by individuals, including individuals who have thyroid disease or various thyroid-related disorders. Thyroid Greens is the first and only goitrogen-free, fluoride-free, gluten free green superfood. The unique combination of the composition is preferably consumed in the form of a beverage. Methods for formulating the supplements described herein are also disclosed below. The unique combination has synergistic advantages over previously known compositions. One such advantage is the lack of goitrogens, which can harm the thyroid hormone production by competing for iodine. Other drinks on the market can include goitrogens, which over time may reduce thyroid hormone production by interfering with iodine uptake in the thyroid gland.

In a preferred embodiment, the composition is comprised of organic *chlorella*, organic dulse, organic acai, organic carrot, organic pineapple, apple pectin, organic inulin, PR-4 probiotic strain—preferably "*Bacillus Coagulans*," organic wheat grass, organic beet root, organic ulva, organic evaporated cane juice, natural flavorsweet flavor, sodium chloride, citric acid, organic guar gum, creamy vanilla flavor, natural raspberry flavor, and natural mixed berry flavor. Other ingredients can be included, which can promote healthy thyroid and adrenal glands of the human body as described in detail herein.

More particularly, a preferred embodiment of the present invention comprises from about 800 to 2200 mg of organic *chlorella*, from about 100 to 900 mg of organic dulse, from about 25 to 400 mg of organic acai, from about 50 to 800 mg of organic carrot, from about 50 to 800 mg of organic pineapple, from about 25 to 500 mg of apple pectin, from about 25 to 500 mg of organic inulin, from about 25 to 750 mg of PR-4 probiotic strain—preferably "*Bacillus Coagulans*," from about 50 to 800 mg of organic wheat grass, from about 5 to 200 mg of organic beet root, from about 5 to 150 mg of organic ulva, from about 10 to 5000 mg of organic evaporated cane juice, from about 100 to 800 mg of natural flavorsweet flavor, from about 10 to 300 mg of sodium chloride, from about 5 to 150 mg of citric acid, from about 15 to 250 mg of organic guar gum, from about 50 to 350 mg of vanilla flavor, from about 10 to 400 mg of natural berry flavor, and from about 150 to 900 mg of second natural flavor. The vanilla flavor can be creamy, dried particles, in the form of an extract, or another form. The natural berry flavor can be a raspberry flavor, a strawberry flavor, a blueberry flavor, a blackberry flavor, cranberry flavor, gooseberry flavor, black currant flavor, goji berry flavor, grape flavor, red currant flavor, honeysuckle flavor, or other suitable berries. The second natural flavor can be a combination of at least two of the berry flavors, or can be another flavor, like chocolate, caramel, coconut, lemon, lime, citric, etc., or combinations thereof.

In a preferred embodiment, the composition described above is substantially free from goitrogens and fluorides. In a most preferred embodiment, the composition described above is completely free from goitrogens and fluorides. In some embodiments, the composition can include less than about 1% by weight of goitrogens and/or less than 1% by weight of fluorides. In some embodiments, no goitrogens can be added to the composition.

In one embodiment, the composition described above is provided as a dietary supplement in capsule, tablet or chewable lozenge. In some embodiments, the supplement can be consumed in the form of a beverage or energy shot. In some embodiments, the supplement can be administered in the form of a food item such as a snack bar, wafer or chew. In a preferred embodiment, the supplement can be provided by way of a powdered greens formula, which can be mixed with water or juice (or added to smoothies or other beverages) so that all the ingredients can be consumed as a beverage.

In further embodiments, the supplement can include one or more palatability agents or otherwise has a flavor desirable for human consumption. One exemplary flavor is "mixed berry." In further embodiments, the superfood supplement can include grasses, fruits or probiotics different than or in addition to those described here.

An aspect of the invention is a composition. The composition includes *chlorella*, dulse, acai, carrot, pineapple, apple pectin, inulin, PR-4 probiotic strain, wheat grass, beet root, ulva, natural flavorsweet flavor, guar gum, creamy vanilla flavor, natural raspberry flavor, and natural mixed berry flavor.

An aspect of the invention is a composition used by a patient with thyroid disease. The composition includes from about 800 to 2200 mg of organic *chlorella*, from about 100 to 900 mg of organic dulse, from about 25 to 400 mg of organic acai, from about 50 to 800 mg of organic carrot, from about 50 to 800 mg of organic pineapple, from about 25 to 500 mg of apple pectin, from about 25 to 500 mg of organic inulin, from about 25 to 750 mg of PR-4 probiotic strain, from about 50 to 800 mg of organic wheat grass, from about 5 to 200 mg of organic beet root, from about 5 to 150 mg of organic ulva, from about 10 to 5000 mg of organic evaporated cane juice, from about 100 to 800 mg of natural flavorsweet flavor, from about 10 to 300 mg of sodium chloride, from about 15 to 250 mg of organic guar gum, from about 50 to 350 mg of creamy vanilla flavor, from about 10 to 400 mg of natural raspberry flavor, and from about 150 to 900 mg of natural mixed berry flavor.

An aspect of the invention is a method to reduce iodine competition for a thyroid hormone. The method includes providing a patient with a composition, wherein the composition includes from about 800 to 2200 mg of organic *chlorella*, from about 100 to 900 mg of organic dulse, from about 25 to 400 mg of organic acai, from about 50 to 800 mg of organic carrot, from about 50 to 800 mg of organic pineapple, from about 25 to 500 mg of apple pectin, from about 25 to 500 mg of organic inulin, from about 25 to 750 mg of PR-4 probiotic strain, from about 50 to 800 mg of organic wheat grass, from about 5 to 200 mg of organic beet root, from about 5 to 150 mg of organic ulva, from about 100 to 800 mg of natural flavorsweet flavor, from about 15 to 250 mg of organic guar gum, from about 50 to 350 mg of creamy vanilla flavor, from about 10 to 400 mg of natural raspberry flavor, and from about 150 to 900 mg of natural mixed berry flavor. The composition is provided to the patient in the form of a capsule or a food item.

An aspect of the invention is a composition. The composition includes *chlorella*, dulse, acai, carrot, pineapple, apple pectin, PR-4 probiotic strain, wheat grass, beet root, and ulva. The composition can further include at least one of flavorsweet flavor, guar gum, inulin, vanilla flavor, a berry flavor, citric acid, evaporated cane juice, or a mixed berry flavor. These and other advantages will be apparent from the disclosure of the invention(s) contained herein. The above-described embodiments, objectives, and configurations are neither complete nor exhaustive. The Summary of the Invention is neither intended nor should it be construed as being representative of the full extent and scope of the present invention.

Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention and the Detailed Description, and no limitation as to the scope of the present invention is intended by either the inclusion or non-inclusion of elements in this Summary of the Invention. Additional aspects of the present invention will become more readily apparent from the Detailed Description.

DETAILED DESCRIPTION

As used herein, the phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being modified in all instances by the term "about". The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials, or acts and the equivalents thereof shall include all those described in the summary of the invention, brief description of the drawings, detailed description, abstract, and claims themselves.

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

Composition:

Organic components are described throughout the Specification. While organic components are preferred, one skilled in the art would understand that conventional components can be used without deviating from the invention.

An aspect of the invention is a drink composition. The drink composition can be used by individuals, including individuals who have thyroid disease. The components of the composition are set forth below.

Organic *Chlorella*

In a preferred embodiment, the composition includes a pre-determined amount of organic *chlorella*. In a preferred embodiment, the composition comprises from about 800 to 2200 mg of organic *chlorella*. In a most preferred embodiment, the composition comprises about 1500 mg of organic *chlorella*, or about 12.91 wt. %. In alternate embodiments, one or more additional digestive enzymes can be included or substituted for DPP-IV. There are more than 250,000 enzymes that can be used. Thus, a complete list cannot be provided. However, some suitable digestive enzymes include, but are not limited to pancreatin, amylase, lipase, protease, bromelain, papain, serrapeptase, nattokinase, and combinations thereof.

Organic Dulse

In a preferred embodiment, the composition includes a pre-determined amount of organic dulse. In a preferred embodiment, the composition comprises from about 100 to 900 mg of organic dulse. In a most preferred embodiment, the composition comprises about 500 mg of organic dulse, or about 4.3 wt. %.

Organic Acai

In a preferred embodiment, the composition includes a pre-determined amount of organic acai. In a preferred embodiment, the composition comprises from about 25 to 400 mg of organic acai. In a most preferred embodiment, the composition comprises about 200 mg of organic acai, or about 1.72 wt. %.

Organic Carrot

In a preferred embodiment, the composition further includes a pre-determined amount of organic carrot. In a preferred embodiment, the composition comprises from about 50 to 800 mg of organic carrot. In a most preferred embodiment, the composition comprises about 500 mg of organic carrot, or about 4.3 wt. %.

Organic Pineapple

In a preferred embodiment, the composition further includes a pre-determined amount of dried organic pineapple. In some embodiments, the dried organic pineapple can be drum dried. In a preferred embodiment, the composition comprises from about 50 to 800 mg of organic pineapple. In a most preferred embodiment, the composition comprises about 500 mg of organic pineapple, or about 4.3 wt. %.

Apple Pectin

In a preferred embodiment, the composition further includes a pre-determined amount of apple pectin. Thus, in a preferred embodiment, the composition comprises from about 25 to 500 mg of apple pectin. In a most preferred embodiment, the composition comprises about 300 mg of apple pectin, or about 2.58 wt. %.

Organic Inulin

In a preferred embodiment, the composition can further include a pre-determined amount of organic inulin. In a preferred embodiment, the composition comprises from about 25 to 500 mg of organic inulin. In a most preferred embodiment, the composition comprises about 300 mg of organic inulin, or about 2.58 wt. %.

PR-4 Probiotic Strain

In a preferred embodiment, the composition further includes a pre-determined amount of PR-4 probiotic strain, preferably "*Bacillus Coagulans*." Hundreds of other strains of probiotics can be used including, but not limited to, *Lactobacillus* species strains, or *Bifidobacterium* species strains. In a preferred embodiment, the composition comprises from about 25 to 750 mg of PR-4 probiotic strain. In a most preferred embodiment, the composition comprises about 200 mg of PR-4 probiotic strain, or about 1.72 wt. %.

Organic Wheat Grass

In a preferred embodiment, the composition further includes a pre-determined amount of organic wheat grass. In a preferred embodiment, the composition comprises from about 50 to 800 mg of organic wheat grass. In a most preferred embodiment, the composition comprises about 500 mg of organic wheat grass, or about 4.3 wt. %.

Organic Beet Root

In a preferred embodiment, the composition further includes a pre-determined amount of organic beet root. Therefore, in a preferred embodiment, the composition comprises from about 5 to 200 mg of organic beet root. In a most preferred embodiment, the composition comprises about 70 mg of organic beet root, or about 0.6 wt. %.

Organic Ulva

In a preferred embodiment, the composition further includes a pre-determined amount of organic ulva. In a preferred embodiment, the composition comprises from about 5 to 150 mg of organic ulva. In a most preferred embodiment, the composition comprises about 35 mg of organic ulva, or about 0.3 wt. %.

Organic Cane Juice

In a preferred embodiment, the composition can further include a pre-determined amount of organic cane juice. In some embodiments, the can juice can be evaporated cane juice. In a preferred embodiment, the composition comprises from about 10 to 5000 mg of organic evaporated cane juice. In a most preferred embodiment, the composition comprises about 3500 mg of organic evaporated cane juice, or about 46.49 wt. %. Some embodiments can be free of sugar (cane juice) and can instead use other sweeteners, such as honey, stevia, monkfruit, xylitol, agave syrup, muscovado sugar, turbinado sugar, black strap molasses, dried coconut sugar, coconut nectar, palm sugar, maple syrup, fruit juice, fruit extract, or the like, and combinations thereof.

Natural Flavorsweet Flavor

In a preferred embodiment, the composition further can include a pre-determined amount of natural flavorsweet flavor. In a preferred embodiment, the composition comprises from about 100 to 800 mg of natural flavorsweet flavor. In a most preferred embodiment, the composition comprises about 430 mg of natural flavorsweet flavor, or about 3.7 wt. %.

Sodium Chloride

In a preferred embodiment, the composition can further include a pre-determined amount of sodium chloride. The sodium chloride can be used as a mixing agent and/or a flavorant. In a preferred embodiment, the composition comprises from about 10 to 300 mg of sodium chloride. In a most preferred embodiment, the composition comprises about 140 mg of sodium chloride, or about 1.21 wt. %. In some embodiments, sodium chloride is not included in the composition.

Citric Acid

In a preferred embodiment, the composition can further include a pre-determined amount of citric acid. The citric acid can be used as a flavor enhancer and/or a natural preservative. In a preferred embodiment, the composition comprises from about 5 to 150 mg of citric acid. In a most preferred embodiment, the composition comprises about 50 mg of citric acid, or about 0.43 wt. %.

Organic Guar Gum

In a preferred embodiment, the composition can further include a pre-determined amount of organic guar gum used as a natural thickener. In a preferred embodiment, the composition comprises from about 15 to 250 mg of organic guar gum. In a most preferred embodiment, the composition comprises about 100 mg of organic guar gum, or about 0.86 wt. %.

Vanilla Flavor

In a preferred embodiment, the composition can further include a pre-determined amount of vanilla flavor. The vanilla flavor can be creamy, dried particles, in the form of an extract, or another form. In a preferred embodiment, the composition comprises from about 50 to 350 mg of creamy vanilla flavor. In a most preferred embodiment, the composition comprises about 150 mg of creamy vanilla flavor, or about 1.29 wt. %.

Natural Berry Flavor

In a preferred embodiment, the composition can further include a pre-determined amount of natural berry flavor. The natural berry flavor can be a raspberry flavor, a strawberry flavor, a blueberry flavor, a blackberry flavor, cranberry flavor, gooseberry flavor, black currant flavor, goji berry flavor, grape flavor, red currant flavor, honeysuckle flavor, or other suitable berries. In a preferred embodiment, the composition comprises from about 10 to 400 mg of natural berry flavor. In a most preferred embodiment, the composition comprises about 220 mg of natural raspberry flavor, or about 1.89 wt. %.

Natural Mixed Berry Flavor

In a preferred embodiment, the composition can further include a pre-determined amount of second natural flavor. The second natural flavor can be a raspberry flavor, a strawberry flavor, a blueberry flavor, a blackberry flavor, cranberry flavor, gooseberry flavor, black currant flavor, goji berry flavor, grape flavor, red currant flavor, honeysuckle flavor, or other suitable berries. In some embodiments, the second natural flavor can be a combination of at least two of the berry flavors, or can be another flavor, like chocolate, caramel, coconut, lemon, lime, citric, etc., or combinations thereof. In a preferred embodiment, the composition comprises from about 150 to 900 mg of second natural flavor. In a most preferred embodiment, the composition comprises about 520 mg of natural mixed berry flavor, or about 4.48 wt. %.

Other

In addition, the composition of a preferred embodiment is substantially free of gluten, wheat, egg, peanuts, tree nuts, dairy, corn, soy, artificial colors, preservatives, fish and shellfish.

According to certain embodiments, the compositions described herein may further be provided with one or more palatability agents. These palatability agents serve to add flavor to the powdered composition so that an effective dosage is easier to be ingested. It is within the scope of the present invention that any safe, flavor enhancing palatability agent or sweeteners (previously discussed) can be used in a composition of the present invention.

Method for Treating

An aspect of the invention is a method to reduce iodine competition in an individual. The method includes providing the patient with the composition. The composition can include from about 800 to 2200 mg of organic *chlorella*, from about 100 to 900 mg of organic dulse, from about 25 to 400 mg of organic acai, from about 50 to 800 mg of organic carrot, from about 50 to 800 mg of organic pineapple, from about 25 to 500 mg of apple pectin, from about 25 to 500 mg of organic inulin, from about 25 to 750 mg of PR-4 probiotic strain, from about 50 to 800 mg of organic wheat grass, from about 5 to 200 mg of organic beet root, from about 5 to 150 mg of organic ulva, from about 100 to 800 mg of natural flavorsweet flavor, from about 15 to 250 mg of organic guar gum, from about 50 to 350 mg of creamy vanilla flavor, from about 10 to 400 mg of natural raspberry flavor, and from about 150 to 900 mg of natural mixed berry flavor. In some embodiments, the composition can include from about 10 to 300 mg of sodium chloride, from about 5 to 150 mg of citric acid, and/or from about 10 to 5000 mg of organic evaporated cane juice. The patient can orally consume the composition in the form of a drink or at least one capsule. If a drink is consumed, then between about 1 teaspoon per about 8 ounces of fluid and about 2 tablespoons per about 8 ounces of fluid of the composition can be consumed by the patient. However, a patient can use as much or as little as desired. The fluid can be any drinkable fluid, including water, juice, a smoothie, milk, tea, coffee, or similar fluids. Preferably, the fluid can be cold, but it is also acceptable for the fluid to be warm, such as in a tea. The composition can be consumed by a patient once a day, or can be consumed twice a day, however, the maximum amount of the composition should not be exceeded. If the capsule(s) is consumed, then between about 1 capsule to about 15 capsules, in some embodiments about 10 capsules of the composition can be provided in capsule form per day. The composition can be consumed by the patient, twice daily, three times daily, one time daily, every other day, every two days, every three days, every four days, every five days, every six days, or weekly.

In some embodiments, the individual can have thyroid disease or related thyroid dysfunctions.

Method for Making the Composition

An aspect of the invention is a method to prepare a composition. The method comprises providing proportional amounts of each material such that the resulting composition results containing from about 800 to 2200 mg of organic *chlorella*, from about 100 to 900 mg of organic dulse, from about 25 to 400 mg of organic acai, from about 50 to 800 mg of organic carrot, from about 50 to 800 mg of organic pineapple, from about 25 to 500 mg of apple pectin, from about 25 to 500 mg of organic inulin, from about 25 to 750 mg of PR-4 probiotic strain, from about 50 to 800 mg of organic wheat grass, from about 5 to 200 mg of organic beet root, from about 5 to 150 mg of organic ulva, from about 100 to 800 mg of natural flavorsweet flavor, from about 15 to 250 mg of organic guar gum, from about 50 to 350 mg of creamy vanilla flavor, from about 10 to 400 mg of natural raspberry flavor, and from about 150 to 900 mg of natural mixed berry flavor. In some embodiments, the composition can include from about 10 to 300 mg of sodium chloride, from about 5 to 150 mg of citric acid, and/or from about 10 to 5000 mg of organic evaporated cane juice. The components are mixed, then can be provided to a delivery device (for example capsule or a powder).

Ranges have been discussed and used within the forgoing description. One skilled in the art would understand that any sub-range within the stated range would be suitable, as would any number within the broad range, without deviating from the invention.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

What is claimed is:

1. A compositing for treating a patient with thyroid disease, comprising:
   1500 mg of *chlorella;*
   150 mg of dulse;
   200 mg of acai;
   500 mg of carrot;
   500 mg of pineapple;
   300 mg of apple pectin
   50 mg of a probiotic blend
   500 mg of wheat grass
   70 mg of beet root;
   35 mg of ulva;
   430 mg of natural flavors;
   140 mg of sodium chloride;
   50 mg of citric acid; and
   100 mg of guar gum; and
   wherein the probiotic blend includes at least one of *Bacillus Coagulans, Lactobacillus* and *Bifidobacterium.*

2. The composition of claim 1, wherein the composition is completely free from goitrogens.

3. The composition of claim 2, wherein the natural flavors are comprised of one or more of a vanilla flavor, a raspberry flavor, and a mixed berry flavor.

4. The composition of claim 3, wherein the *chlorella,* dulse, acai, carrot, pineapple, wheat grass, beet root, and ulva are classified as USDA organic.

5. The composition of claim 4, wherein the composition does not contain a gluten, an egg, a peanut, a tree nut, a dairy, a corn, a soy, an artificial color, a fish, or a shellfish.

6. The composition of claim 5, further comprising at least one palatability agent.

7. The composition of claim 6, wherein the composition comprises at least one digestive agent.

8. The composition of claim 7, wherein the at least one digestive agent is selected from the list consisting of pancreatin, amylase, lipase, protease, bromelain, papain, serrapeptase, nattokinase, and combinations thereof.

9. The composition of claim 1, wherein the composition is provided as a dietary supplement.

10. The composition of claim 1, wherein the composition is provided in the form of a beverage.

11. The composition of claim 1, wherein the composition is provided in the form of a food item.

12. A composition for reducing goitrogenic consumption in a patient with thyroid disease comprising:
    1200 to 1800 mg of *chlorella;*
    100 to 200 mg of dulse;
    100 to 300 mg of acai;
    400 to 600 mg of carrot;
    400 to 600 mg of pineapple;
    200 to 400 mg of apple pectin;
    200 to 400 mg of inulin;
    25 to 75 mg of a probiotic blend;
    400 to 600 mg of wheat grass;
    50 to 100 mg of beet root;
    5 to 75 mg of ulva;
    1000 to 3000 mg of evaporated cane juice;
    300 to 500 mg of natural flavors;
    100 to 200 mg of sodium chloride; and
    75 to 150 mg of guar gum.

13. The composition of claim 12, wherein the composition is provided as a dietary supplement.

14. The composition of claim 12, wherein the composition is provided in the form of a beverage.

15. The composition of claim 12, wherein the composition is provided in the form of a food item.

16. The composition of claim 12, wherein the composition does not contain a gluten, an egg, a peanut, a tree nut, a dairy, a corn, a soy, an artificial color, a fish, or a shellfish.

17. The composition of claim 16, further comprising at least one palatability agent.

18. The composition of claim 17, further comprising at least one digestive agent.

19. The composition of claim 18, wherein the at least one digestive agent is selected from the list consisting of pancreatin, amylase, lipase, protease, bromelain, papain, serrapeptase, nattokinase, and combinations thereof.

20. A method to reduce iodine competition for a thyroid hormone comprising:
    administering to a patient in need thereof a composition, wherein the composition comprises:
    1200 to 1800 mg of *chlorella;*
    100 to 200 mg of dulse;
    100 to 300 mg of acai;
    400 to 600 mg of carrot;
    400 to 600 mg of pineapple;
    200 to 400 mg of apple pectin;
    200 to 400 mg of inulin;
    25 to 75 mg of a probiotic blend;
    400 to 600 mg of wheat grass;
    50 to 100 mg of beet root;
    5 to 75 mg of ulva;
    1000 to 3000 mg of evaporated cane juice;
    300 to 500 mg of natural flavors;
    100 to 200 mg of sodium chloride; and
    75 to 150 mg of guar gum,
    wherein the composition is administered to the patient in the form of a capsule or a food item.

21. The method of claim 20, wherein the composition is administered to the patient in the form of the capsule, and wherein between about 1 capsule and about 15 capsules of the composition is administered to the patient.

22. The method of claim 20, wherein the composition is administered to the patient in the form of the food item, and wherein between about 1 teaspoon and about 1 tablespoon of the composition is administered to the patient.

23. The method of claim 20, wherein the composition is administered to the patient between three times a day and once a week.

24. The method of claim 20, wherein the composition is administered to the patient in the form of the food item, and wherein the food item is a drink.

25. The method of claim 24, wherein a fluid of the drink is selected from the group consisting of a juice, a water, a milk, a smoothie, a tea, and a coffee.

* * * * *